United States Patent [19]
Barreras

[11] Patent Number: 5,807,397
[45] Date of Patent: *Sep. 15, 1998

[54] IMPLANTABLE STIMULATOR WITH REPLENISHABLE, HIGH VALUE CAPACITIVE POWER SOURCE AND METHOD THEREFOR

[75] Inventor: Francisco J. Barreras, Miami, Fla.

[73] Assignee: Plexus, Inc., Miami, Fla.

[ * ] Notice: The portion of the term of this patent subsequent to Jan. 4, 2015, has been disclaimed.

[21] Appl. No.: 672,328

[22] Filed: Aug. 1, 1996

Related U.S. Application Data

[63] Continuation-in-part of Ser. No. 368,326, Jan. 4, 1995, Pat. No. 5,591,217.

[51] Int. Cl.$^6$ .................................................. A61N 1/18
[52] U.S. Cl. .............................................................. 607/61
[58] Field of Search .............................. 607/30, 32, 33, 607/61

[56] References Cited

U.S. PATENT DOCUMENTS

| | | |
|---|---|---|
| 3,209,081 | 9/1965 | Ducote et al. . |
| 3,258,013 | 6/1966 | Druz . |
| 4,082,097 | 4/1978 | Mann et al. ............................. 607/33 |
| 4,102,344 | 7/1978 | Conway et al. . |
| 4,406,288 | 9/1983 | Horwinski et al. . |
| 4,408,607 | 10/1983 | Maurer . |
| 4,408,608 | 10/1983 | Daly et al. . |
| 4,424,812 | 1/1984 | Lesnick . |
| 4,556,061 | 12/1985 | Barreras et al. . |
| 4,612,934 | 9/1986 | Borkan . |
| 4,690,144 | 9/1987 | Rise et al. . |
| 4,702,254 | 10/1987 | Zabara . |
| 5,312,439 | 5/1994 | Loeb ........................................... 607/2 |
| 5,324,316 | 6/1994 | Schulman et al. ........................ 607/61 |
| 5,358,514 | 10/1994 | Schulman et al. ........................ 607/61 |
| 5,405,367 | 4/1995 | Schulman et al. ........................ 607/61 |

OTHER PUBLICATIONS

Pacing and Clinical Electrophysiology, Aug. 1988, vol. 11, No. 8, pp. 1117–1247.
Panasonic, Technical Guide of Electric Double Layer Capacitors.

*Primary Examiner*—Scott Getzow
*Attorney, Agent, or Firm*—Robert C. Kain, Jr.

[57] ABSTRACT

The implantable stimulator in accordance with the principles of the present invention utilizes a high value, small sized capacitor having at least a capacitive rating of 0.1 farads which is completely contained within the implantable stimulator. This high value, small size capacitor or series of capacitors enables the implantable stimulator to deliver, on a controlled and continual basis, electric stimulation pulses to targeted tissues over at least an 8 hour period. Further, the capacitive power source is replenished via an external, RF coupled device on a daily or other long term periodic basis. During the replenishing cycle, the energy contained in the battery of the external transmitter is transferred to the internal capacitive power source in the implantable stimulator. The method includes providing, on an exclusive basis, power to an implantable stimulator via a high value capacitive source during at least an 8 hour cycle of substantially continual delivery of electric stimulation pulses to targeted tissue. The method includes incorporating and containing a capacitive device in the implantable stimulator wherein the capacitive device has a capacitive rating of at least 0.1 farads. The capacitive device captures and stores a predetermined amount of coulombs of electrical energy. This electrical energy is utilized to power the implantable stimulator during at least an 8 hour cycle during substantial continual delivery of electric stimulation pulses, all based upon energy stored by the capacitive device. Longer cycles (exceeding 24 hours) may be possible. The replenishment unit can be programmed to interrogate the implant and reprogram the implant upon detection of a lower power status signal. Also, automatic as well as manually commanded replenishment routines are established between the replenishment unit and the implant. Data transmission, error detection routines are established for the programming of the implant.

17 Claims, 7 Drawing Sheets

IMPLANTABLE STIMULATOR WITH REPLENISHABLE, HIGH VALUE CAPACITIVE POWER SOURCE AND METHOD THEREFOR

This is a continuation-in-part of U.S. patent application Ser. No. 08/368,326, filed Jan.4, 1995, now U.S. Pat. No. 5,591,217.

The present invention relates to an implantable stimulator which includes a high value capacitive power source (exceeding 0.1 farads) and a method to power the implantable stimulator on an exclusive basis during continual delivery of electrical stimulation pulses.

BACKGROUND OF THE INVENTION

Implantable tissue stimulators are utilized to deliver a train of low voltage level electrical pulses to specific nerves or muscles via an implanted lead. Implantable stimulators have been utilized to stimulate nerves in the spinal cord (paresthesia), to stimulate the bladder and control bladder functions, to stimulate the sphincter in control of that bodily function, and to stimulate the brain (for example, to control epileptic episodes). Other implantable devices provide diagnostic monitoring of a patient's condition as well as the delivery of drugs subcutaneously (such as an insulin pump).

With respect to spinal control stimulation nerves in the spinal cord are electrically stimulated with low voltage level, controlled electric current pulses delivered directly on or at the nerve via an implanted lead or leads in order to achieve paresthesia. Spinal cord stimulation is utilized to treat chronic pain of the trunks and limbs as well as for intractable chest angina. For example, spinal cord stimulation has been utilized to treat peripheral vascular disease (PVD).

With respect to all of these implantable stimulators and devices, it is necessary to provide power to the device implanted below the skin. Since the device is subcutaneously implanted in a patient, the power source must support stimulator or device operation for a reasonable period of time in order to reduce further surgical trauma to the patient. If the device cannot operate under its own power, the device must be surgically removed to replace or recharge the power source therein.

Stimulators can be classified in three general areas: radio frequency or RF coupled and powered stimulators, battery powered stimulators and stimulators which combine RF coupling and battery powered systems. The term battery means an electrochemical (primary or secondary) power system.

The RF coupled and powered stimulator does not carry or contain an independent power source. Therefore, the RF coupled stimulator requires an external RF transmitter and a surgically implanted receiver. The RF link transfers stimulation pulses percutaneously through the skin and adjacent tissue layers of the patient from the external RF transmitter to the surgically implanted RF receiver and stimulator device. The transmitter sends stimulation pulses to be applied ultimately to the implanted electrodes plus programming data defining the polarity of each electrode relative to each other to the implanted stimulation device. The implanted receiver obtains these stimulation pulses and programming data, converts the pulses as necessary, delivers the energy contained in each transmitted stimulation pulse to the implanted electrodes as defined by the programming data. The stimulation pulses are inductively coupled emf waves from the external transmitter to the implanted receiver. The common disadvantage of the RF coupled and powered stimulator is that the patient must always wear the external transmitter and antenna (even during sleep) in order for the implanted receiver to deliver stimulation pulses to the targeted tissue. Stimulation therapy ceases the moment the transmitter antenna is withdrawn just a few inches away from the implanted receiver. Although the RF powered and coupled stimulator has this disadvantage, the service life of such an RF coupled and powered stimulator is not limited to the life of a battery contained within a fully implantable stimulation unit. Accordingly, the long term cost of the RF coupled and powered stimulators is less than the battery powered stimulators because the service life of the former is much longer than that of the latter. RF coupled and powered stimulators have been commercially marketed by Medtronics of Minneapolis, Avery laboratories of New York and Neuromed of Fort Lauderdale, Fla.

The battery powered stimulator utilizes a primary, non-rechargeable battery as a power source to power the implanted stimulator. This battery will operate without requiring an external transmitter to recharge or replenish the battery in the implantable stimulator. The battery provides sole and exclusive power to the implanted stimulator continually while the stimulator generates one or more electric stimulation pulses, in a controlled manner, to the target tissue. Of course, the stimulation pulses are delivered to the targeted tissue via implanted leads. An external programmer may be used to non-invasively adjust the stimulation parameters or control values in the implanted stimulator. Programming may be provided through an RF telemetry link. After programming, the stimulator remembers the parameter values (the values are stored in an electronic memory) as long as the battery voltage remains above a minimum voltage level required by the electronics. Unfortunately, the service life of these battery powered stimulators is limited to the battery life. Accordingly, it is necessary to surgically remove and then replace the battery powered implantable stimulators upon depletion of the electrochemically active materials in the battery. This disadvantage (i.e. surgical replacement) increases its long term cost to the patient relative to the aforementioned RF coupled and powered stimulators. The battery powered implantable stimulators do not require an external transmitter to deliver the stimulation electrical pulses. Accordingly, the battery powered implantable stimulators are easier to use and more comfortable than the RF coupled and powered stimulators. Battery powered stimulators have been marketed by Medtronics of Minneapolis, Neuromed of Ft. Lauderdale and Exonix of Miami.

The third category of implantable stimulators include stimulators which combine the RF coupling and powered delivery systems with the battery powered implantable stimulator technology. These types of stimulators enable the patient to carry the implantable stimulator without the necessity of having an external RF coupled unit proximate the implant at all times. However, the stimulator must be surgically replaced after the battery is depleted if use of the external RF transmitter is not desired. This type of stimulator allows RF coupled stimulation at times when wearing the external transmitter is not objectionable, thereby extending battery life. Also, this type of stimulator may allow for continuing RF coupled stimulation after the internal power source is depleted, although some of these RF coupled and battery powered implantable stimulators do not operate if the battery is completely depleted in the implanted stimulator.

U.S. Pat. No. 4,612,934 to Borkan discloses a non-invasive multi-programmable tissue stimulator. The Borkan implantable stimulator includes an external transmitter which transfers power percutaneously through an RF coupling to an implanted stimulator. The implanted stimulator does include a voltage storage circuit and a battery. The voltage storage circuit stores a minimal amount of voltage and electrical energy. Particularly, the Borkan disclosure provides "[t]he output of the detector circuit 22 is stored as voltage Vm in the voltage storage circuit 36 which comprises diode 80, capacitor 82, optional zener diode 83 and resistor 84. Alternatively, a rechargeable voltage source could be substituted for capacitor 82." Column 14, lines 5–9. Obviously, capacitor 82 is used as a filter device and not as a power source. The long term voltage stored in this circuit Vm is applied to a comparator and, when voltage Vm is less than a predetermined reference voltage, the implantable stimulator "goes to sleep," that is, the implantable stimulator stops delivering stimulation pulses to the targeted tissue. The implantable stimulator is "woken up" or activated upon receipt of RF coupled commands in a certain sequence. Accordingly, the voltage storage circuit in the Borkan disclosure simply acts as a temporary voltage storage unit to detect the presence of the RF transmitter and not a long term power supply for the implanted stimulator. The Borkan stimulator is utilized to stimulate tissue for various neurological and muscular disorders.

U.S. Pat. No. 4,690,144 to Rise discloses a wireless transcutaneous electrical tissue stimulator which deliver stimulation pulses to the surface of the patient's skin. It appears that the Rise transcutaneous stimulator is battery powered stimulator controlled by a wireless remote control. The Rise transcutaneous tissue stimulator is utilized to relieve pain and stimulate muscles as necessary.

U.S. Pat. No. 4,424,812 to Lesnick discloses an implantable, externally programmable, microprocessor-controlled tissue stimulator. The Lesnick disclosure does not describe in detail the electrical energy storage device in the implanted stimulator. However, it is apparent that an internal battery is utilized within the Lesnick implantable stimulator. The external RF coupled device is utilized only to program the implantable stimulator. The patient turns on and off the implanted stimulator by placing and removing a hand held magnet which in turn opens and closes a reed switch in the implantable stimulator.

U.S. Pat. No. 4,406,288 to Horwinski discloses a bladder control device and a method therefor. Basically, an implantable stimulator is utilized to stimulate the pelvic muscles and to control the bladder. The implantable stimulator uses a internal battery as an energy storage device.

U.S. Pat. No. 4,702,254 to Zabara discloses a neurocybernetic prosthesis. The preferred embodiment incorporates a battery and associated circuitry in a fully implantable enclosure. An RF coupled powered device is also discussed.

U.S. Pat. No. 4,556,061 to Barreras discloses a cardiac pacer with a battery consumption monitor circuit. This pacing unit, embodied as an implantable stimulator of the heart, utilizes a battery.

U.S. Pat. No. 4,408,607 to Maurer discloses an implantable device powered by a capacitor 20 (Maurer FIGS. 1 & 2). However, the Maurer disclosure states "[i]t is a characteristic of these capacitors that their rating voltage must not be exceeded, otherwise excessive out-gassing and even explosion will occur." col. 3, lines 22–25. The capacitor power source in the implantable device is charged by an external RF coupled transmitter or power coil system (Maurer 23 and 32). The RF coupled power is applied to a regulator, an overvoltage inhibitor, and a pressure override (Maurer 24, 25 and 27). The output of the pressure override circuit is fed to a diode which charges the capacitor (Maurer 20). To avoid overcharging, a comparator in the overvoltage inhibitor compares the charging voltage to a predetermined voltage level. When the charging voltage exceeds the set level, the charging current is shunted to ground via resistor (Maurer 64). A further embodiment in the Maurer '607 patent disclosure utilizes a lithium battery 81 (Maurer FIGS. 3 & 4). The battery is switched-in during the charging cycle in order to continue the delivery of stimulation pulses to the patient.

The Maurer '607 patent disclosure utilizes capacitors which are subject to out gassing. col. 3, lines 22–25. Hence, the capacitors in the '607 patent disclosure must be electrochemical devices. Further, '607 patent disclosure does not specify a certain volumetric size for the capacitor, a capacitive rating of 0.1 farads or higher for the Maurer capacitor, and does not identify a discharge or load factor.

U.S. Pat. No. 4,102,344 to Conway et al. discloses an implantable device that is activated and powered exclusively by an external high frequency transmitter. The Conway '344 patent disclosure states "[i]t will be recalled that the 300 kilohertz output to the oscillator 24 is interrupted by trigger generator 24 for 1½ milliseconds every 50 milliseconds. Whenever this happens, the receiver coil 26 no longer picks up a signal and the voltage across terminals 40 and 41 drops to zero." Column 4, lines 55–60. "While there is no longer voltage between conductors 42 and 43, [which are directly electrically connected to terminals 40 and 41], the capacitor 52 has a voltage thereacross, the polarity of which is such that the right hand terminal thereof which is connected to the collector of transistor 49 through the electrode leads 11 and 12 and a portion of the bladder tissue, is positive with respect to the left hand terminal of the capacitor." Column 5, lines 2–8. "Capacitor 52 will continue to discharge for approximately 1½ milliseconds, the period of interruption of the output of oscillator 22. After the interruption, the oscillator 22 again provides an output which is applied to transmitter coil 23 and is inductively picked up by transmitter coil 22. Again a voltage appears across conductors 42 and 43 to cause a voltage drop across the resistor 45." Column 5, lines 13–20.

The Conway '344 patent disclosure includes two separate storage capacitors (Conway storage capacitors 31 and 30 as shown in FIG. 4). These capacitors are equivalent to other capacitors shown in FIG. 5 of Conway (Conway capacitors 62 and 69). "The purpose of providing two separate circuits from the power supply to energize electrode leads 11 and 12 on the one hand and 13 and 14 on the other is to insure against any current path being established from bipolar electrode 17 through the bladder tissue to bipolar electrode 18. As will be clear from the subsequent description, there is one current path between electrode leads 11 and 12 and a completely separate current path between electrode leads 13 and 14." Column 5, lines 36–45. In the summary of the Conway '344 patent disclosure, "[i]t will be noted that in each of three modifications, the storage capacitor is discharged by reason of the received voltage being temporarily terminated. It is thus not necessary to provide any special triggering means for triggering a transistor or SCR." Column 8, lines 61–65.

The capacitor-energy storage device in the Conway '344 patent disclosure does not provide power on an exclusive basis over an 8 hour period unless the external transmitter and oscillator 22 is continuously placed near or adjacent the receiving coil in the implant during that time period.

U.S. Pat. No. 5,312,439 to Loeb discloses an implantable device having an electrolytic capacitive storage electrode.

The device utilizes exposed electrolytic electrodes. (Loeb electrodes 11 and 12 shown in FIG. 1). "Electrodes 11 and 13, when immersed in body fluids, provide a very large capacitance between them. Such capacitance is represented at 15 and may easily be on the order of a hundred or so microfarads." Column 3, lines 44–47. Although the schematic in Loeb FIG. 1 also identifies Loeb capacitor 9, the detailed description in the Loeb '439 patent disclosure does not identify that the aforementioned capacitor provides significant electrical energy storage for the device. The description states that Loeb's electrode 11 "will easily store 100 microcoulombs of charge. Only 3.84 microcoulombs is required for a 15 ma stimulating pulse having a 256 microsecond duration." Column 5, lines 62–65. Further, the Loeb '439 patent disclosure utilizes other capacitors (Loeb capacitors 37 and 39). "From that detected signal, a short term detected signal is obtained by resistor 36 and capacitor 37 [in FIG. 5] and a long term average detected signal is obtained by resistor 38 and capacitor 39 (which have a longer time constant than the first resistor and capacitor). The short term detected signal and the long term average detected signal are fed into comparator 40 which provides the detected data . . ." Column 6, lines 51–59. It is clear from this description that Loeb capacitors 37 and 39 act as filters for the detected data signal.

U.S. Pat. No. 5,324,316 to Schulman et al. discloses an implantable microstimulator which has one or more electrodes immersed in body fluids. The capacitor formed by the body fluids and the electrodes stores 100 microcoulombs of charge. See column 6, lines 44–50. Schulman capacitor 23 in FIGS. 3, 4, 5 and 11 is used to tune the circuit which includes a coil. See column 6, lines 60–63, column 8, lines 16–17, column 13, lines 20–24. Schulman capacitor 24 in FIG. 3 smooths out the ripple and is used as a filter. Column 7, lines 6–7. The Schulman '316 patent disclosure provides for a "method of controlling the amount of energy received and stored by the microstimulator would be by connecting a voltage regulator in place of regulator 25, to switch a capacitor in and out of circuit and parallel with capacitor 23." Column 7, lines 20–24. This describes a filtering type of capacitor. Schulman capacitors 27 and 32 are utilized to detect the short term detected signal and the long term average detected signal. Column 7, lines 44–47. The electrolytic capacitor exposed to the body fluid has a capacitive rating of 10 or 15 microfarads. Column 8, lines 10–11. In Schulman FIG. 11, capacitor 78 is utilized to smooth the received signal. Column 13, lines 20–25.

U.S. Pat. No. 5,358,514 ('514 patent) to Schulman discloses an implantable medical stimulator. The implantable stimulator includes a capacitor (Schulman capacitor 20 as shown in FIGS. 2 and 6). However, the Schulman '514 patent discloses no details regarding the capacitive rating or volumetric size of that capacitor. For example, in column 10, lines 55–60, the Schulman '514 patent disclosure simply identifies that the capacitor holds a charge which is controlled by logic and a control switch (Schulman logic 16 and switch 17). The disclosure does identify that a self-attaching electrode could be used with a porous structure and an anodized layer as an electrolytic capacitor in lieu of the capacitor. Column 11, lines 55–60. The capacitance of the external electrolytic capacitor is on the order of 2 to 30 microfarads. Column 11, line 63. In describing the aforementioned capacitor, the disclosure states "[s]uch discrete capacitor, constructed in accordance with integrated circuit fabrication techniques known in the art, occupies a substantial amount of space within the microdevice." Column 12, lines 13–16. "In operation of the microdevice as microstimulator, the storage capacitor 20 is charged to a suitable stimulating voltage. Upon discharge, or partial discharge of the charge, as controlled by the closing of the switch 18 and by the setting of the current amplitude limiter 19 (FIG. 2), an electrical current pulse flows between the two electrodes 14 and 15, thereby stimulating the nerve 100." Column 13, lines 11–18. See also column 17, lines 8–12.

U.S. Pat. No. 5,405,367 to Schulman ('367 patent disclosure) discloses the use of a capacitor, (Schulman capacitor 20 in FIG. 2) which is provided by electrodes (Schulman 15 and 14), on the order of 2 to 30 microfarads. Column 5, lines 52–55. In Schulman FIG. 9, a discrete capacitor (Schulman 50) is located inside the implant. "Such discrete capacitor, constructed in accordance with well-known art, would occupy a substantial amount of space within the microstimulator in order to achieve the same capacitance as the sintered electrode." Column 5, lines 65–69. The electrolytic capacitor is again discussed at column 6, lines 8–9. "The electric stimulation occurs through discharge of electrolytic capacitor 20, FIG. 2 . . . " Column 11, lines 22–23. The use of an additional internal capacitor is discussed at column 12, lines 46–51. Single capacitors made or classified as electrolytic, axial, tantalum capacitors "or other suitable, miniature capacitors which are readily commercially available" (column 13, lines 7–10), are identified in conjunction with an axial capacitor (Schulman capacitor 50 in FIG. 9).

U.S. Pat. No. 3,258,013 to Druz ('013 patent disclosure) discloses a defibrillator which "is operable from a wholly self-contained battery power source 10 . . . " Column 3, lines 63–65. Shunt condensers or capacitors (Druz capacitors 36 and 37 FIG. 1) are part of a two section lumped constant, delay line. Column 4, lines 30–33. The delay line discharge pulsing circuit (Druz circuit 15) is fully charged to the desired voltage. Column 5, lines 28–30. A condenser or capacitor (Druz item 45) is a filter and is used in combination with a resistor. Column 5, line 36. The delay line discharge pulsing circuit "is employed as the energy storage device, with at least two inductance-capacitance sections as shown in FIG. 1 . . . " Column 7, lines 43–45. The delay line discharge pulsing circuit has a characteristic impedance of approximately 100 ohms and delivers a current impulse corresponding to an energy range from 60–100 watt-seconds. Druz describes certain capacitors as being 20 microfarads each (capacitors 36 and 37). Column 8, line 6. The preferred embodiment delivers a threshold defibrillation pulse of 6.5 amperes and peak current of 10 amperes over an interval of 8.5 milliseconds.

U.S. Pat. No. 3,209,081 ('081 patent disclosure) to Ducote discloses an implant with "power supplied to amplifier transistors 15 and 16 of the implanted radio receiver F from a power transmitter, indicated at D." Column 3, lines 1–3. The electrical potential delivered through the RF signal is stored in a capacitor (Ducote capacitor 20). Column 3, line 11. Voltage is applied to that capacitor "continuously and constantly . . . as long as the power transmitter D is functioning." Column 3, lines 16–17. "With the use of the power supply herein described, same could be implanted in the body of the patient and supplied with power from a transmitter externally of the body without physical connection." Column 4, lines 55–57.

U.S. Pat. No. 4,408,608 to Daly ('608 patent disclosure) discloses an implantable stimulator. Daly's capacitor C1 is used to tune in coil L1 in FIG. 1. Column 6, line 64 through column 7, line 1. Daly's capacitor C2 is used to filter the output of the rectifier circuit. Column 7, lines 11–12. Daly's capacitor C3 and resistor R1 are used to determine rise and fall times in the ripple and are used to develop a control signal. Column 7, lines 30–32. Daly's capacitor C4 is charged based upon the output of data/power separator 10. Column 7, lines 35–36. "In the presence of an RF carrier, capacitor C4 charges through resistor R2 to the switching threshold of Schmitt trigger ST2. When the capacitor charges to the threshold level of the Schmitt trigger, its NODATA output goes high to control a reset of the counter and the selection of channel zero." Column 7, lines 53–57. "Whenever there is a break in the carrier transmission, i.e., data is being transmitted because the end of a pulse has been detected, the output of Schmitt trigger ST1 goes low, and the output of invertor 14 goes high. This causes transistor FET1 to turn on and to discharge capacitor C4." Column 7, lines 63–67. "[S]oon after capacitor C4 starts to charge at the start of a data pulse, it is discharged with the arrival of a data break, the end of the pulse, when transistor FET1 turns on." Column 8, lines 4–7. Capacitor C2 powers logic elements. Column 9, lines 27–29. "Capacitor C2, in addition to serving as a filter for the power supply, provides the additional function of power-down detection." Column 11, lines 57–59.

OBJECTS OF THE INVENTION

It is an object of the present invention to provide an implantable stimulator with a replenishable, high value capacitive power source. Capacitors do not suffer a significant wear out during charge and discharge cycles as rechargeable batteries do.

It is another object of the present invention to provide a method of supplying power, on an exclusive basis, during at least an 8 hour cycle of substantially continually delivery of electric stimulation pulses utilizing a high value capacitor.

It is a further object of the present invention to provide an implantable stimulator which can be operated for a significant period of time using the energy stored in a high value capacitor (exceeding 0.1 farads).

It is a further object of the present invention to provide an implantable stimulator with a capacitive power source utilizing a plurality of high value capacitors electrically connected in parallel.

It is a further object of the present invention to utilized this high value capacitive power source in combination with an implantable stimulator.

It is further object of the present invention to non-invasively fully replenish the capacitive power source within 30 minutes or less.

It is a further object of the present invention to utilize a high value capacitive power source in conjunction with diagnostic RF coupled data transmitter and receiver devices implanted in the patient.

It is another object of the present invention to provide a drug delivery system utilizing a replenishable, high value capacitive power supply.

It is an additional object of the present invention to provide an interactive data transfer protocol between the programming unit and the implant to significantly reduce or eliminate transmission errors.

It is an additional object of the present invention to provide a communications protocol with an echo transmission check routine.

It is an additional object of the present invention to provide an interactive data communication through a titanium encased implant unit.

It is an additional object of the present invention to provide replenishing power via an inductive emf power link between the replenishment unit and the implant and through the titanium encasement of the implant.

It is an additional object of the present invention to permit the patient to control certain stimulation pulses generated by the implant.

It is an additional object of the present invention to permit the patient to increase either the duration or the current level of the stimulation pulses via the replenishment unit.

It is an additional object of the present invention to permit user actuated charging or replenishment of the capacitive power supply in the implant or automatic replenishment based upon a telemetric inquiry by the replenishment unit directed at the implant.

It is an additional object of the present invention to permit the replenishing unit to reprogram the implant upon detection of a "memory loss" or other similar low power status value in the implant.

It is a further object of the present invention to provide an implant that monitors the charge level of the capacitive power source.

It is another object of the present invention to provide circuitry which prevents overcharging of the capacitive power source.

It is an additional object of the present invention to provide an implant that communicates with the replenishment unit to turn off the EMF power transmissions when the capacitive power source is fully charged.

It is another object of the present invention to re-start the EMF power transmissions in the replenishment unit when the implant determines that the capacitive power source has reached a minimum charge level.

SUMMARY OF THE INVENTION

The implantable stimulator in accordance with the principles of the present invention utilizes a high value, small sized capacitor having at least a capacitive rating of 0.1 farads which is completely contained within the implantable stimulator. This high value, small size capacitor or series of capacitors enables the implantable stimulator to deliver, on a controlled and continual basis, electric stimulation pulses to targeted tissues over at least an 8 hour period. Further, the capacitive power source is replenished via an external, RF coupled device on a daily or other long term periodic basis. During the replenishing cycle, the energy contained in the battery of the external transmitter is transferred to the internal capacitive power source in the implantable stimulator. The method includes providing, on an exclusive basis, power to an implantable stimulator via a high value capacitive source during at least an 8 hour cycle of substantially continual delivery of electric stimulation pulses to targeted tissue. The method includes incorporating and containing a capacitive device in the implantable stimulator wherein the capacitive device has a capacitive rating of at least 0.1 farads. The capacitive device captures and stores a pre-determined amount of coulombs of electrical energy. This electrical energy is utilized to power the implantable stimulator during at least an 8 hour cycle during substantial continual delivery of electric stimulation pulses, all based upon energy stored by the capacitive device. Longer cycles (exceeding 24 hours) may be possible.

The replenishment unit can be programmed to interrogate the implant and reprogram the implant upon detection of a lower power status signal. Also, automatic as well as manually commanded replenishment routines are established between the replenishment unit and the implant. Data transmission, error detection routines are established for the programming of the implant.

BRIEF DESCRIPTION OF DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENTS

The present invention relates to a method and an apparatus for an implantable stimulator with a replenishable, high value, capacitive power source. Particularly, this high value capacitive power source could be embodied as a single high value capacitor or a plurality of parallel connected high value capacitors. One type of high value, small size capacitors is sold by Panasonic as Model No. 641. The Panasonic capacitor has a diameter of approximately 18 millimeters and a thickness of approximately 4 millimeters. Accordingly, these capacitors have a volumetric size of less than 4.0 cubic centimeters. This Panasonic model capacitor has a capacitive rating of 1.0 farads. The typical size of the implantable stimulators is 5 centimeters by 6 centimeters by 1 centimeters (that is, 30 cubic centimeters). The benefit of using these high value, small size capacitive energy storage units is that the energy storage is not an aqueous or water-based system.

Prior art implantable stimulators utilize nickel-cadmium rechargeable batteries. These batteries store energy in an aqueous system and the energy storage mechanism is an electrochemical reaction. Further, these nickel cadmium batteries release hydrogen gas which adversely affect the performance of the stimulator and compromise the patient's well being.

The high value, small sized capacitive energy storage source utilized in the present invention are small, light weight and chemically inert. Further, the electrical storage mechanism is a physical phenomena and not electrochemical reaction as is the case with nickel cadmium batteries or other rechargeable batteries.

These capacitors are classified as low internal impedance, low power loss and high charge rate capacitors.

Figure 1:
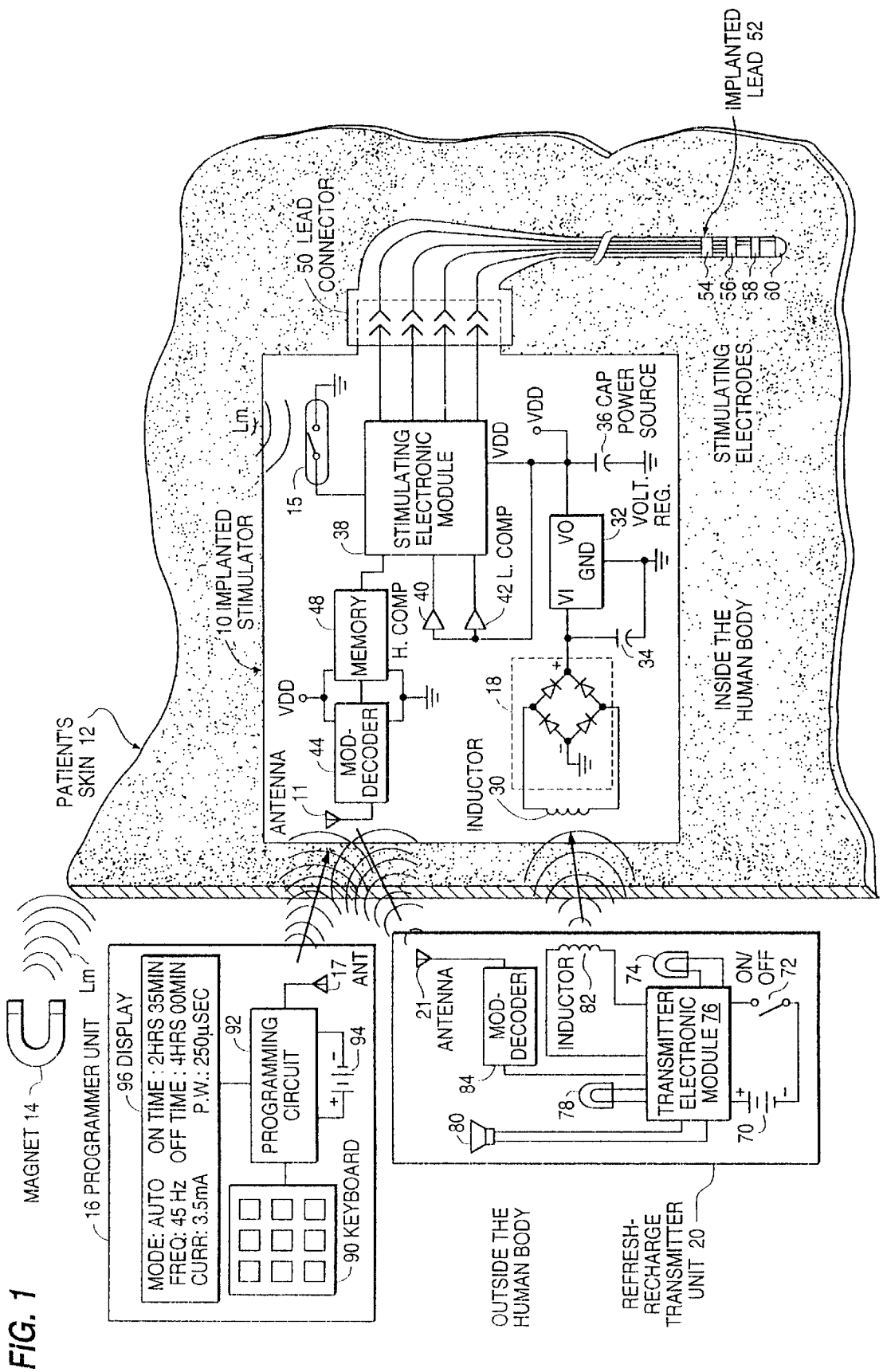
FIG. 1 diagrammatically illustrates the implanted stimulator, the hand held magnet (patient control), the programmer unit (RF coupled to the implanted stimulator) and the refresh-recharge transmitter unit (RF coupled to stimulator)

FIG. 1 illustrates stimulator 10 implanted subcutaneously with respect to a patient's skin 12. A magnet 14 is utilized by the patient to deliver electromagnetic force waves (EMF waves) identified in FIG. 1 as waves Lm. These EMF waves Lm open and close a reed switch 15 mounted within the casing of implantable stimulator 10. The magnet is used by the patient to start/stop stimulation. As stated earlier, the implantable stimulator occupies approximately 60 cubic cm. and is sized roughly 5 cm by 6 cm by 2 cm. FIG. 1 also illustrates a programmer unit 16 and a refresh-replenish transmitter unit 20. Programmer unit 16 and refresh-recharge transmitter unit 20 are coupled via radio frequency (RF) waves to the implantable stimulator 10. However, command signals from either programmer unit 16 or refresh-replenish transmitter unit 20 are sent and received via antennas 17 and 21, respectively. Preferably, refresh-recharge transmitter unit 20 is not used concurrently with programmer unit 16. In any event, an RF telemetric data link is established between antennas 17, 21 and internal antenna 11 in the implanted stimulator 10 when either the programmer unit 16 or refresh-recharge unit 20 is placed in close proximity to implanted stimulator 10.

The major components of implanted stimulator 10 include an inductor receiver coil 30, a full rectifier bridge 18 (consisting of a plurality of diodes) coupled to a voltage regulator 32. A small size capacitor 34 is utilized to smooth the input voltage VI input fed into voltage regulator 32. The output voltage VD of regulator 32 is applied to capacitive energy power supply and source 36 which establishes source power VDD. This source power is applied to stimulating electronic module 38, high threshold comparator 40, low threshold comparator 42, modulator/demodulator and decoder circuit 44 and memory unit or programmable device 48. The output of stimulating electronic module 38 is applied to lead connector 50 and lead connector 50 supplies electric stimulation pulses to implanted lead 52. In a preferred embodiment, implanted lead 52 has plurality of linear electrodes or terminals 54, 56, 58 and 60. Implanted lead 52 is placed on or near targeted tissue such as heart tissue, nerves in the spinal cord, muscles in the bladder or sphincter, or wherever electrical pulses are required to stimulate tissue.

Figure 6:
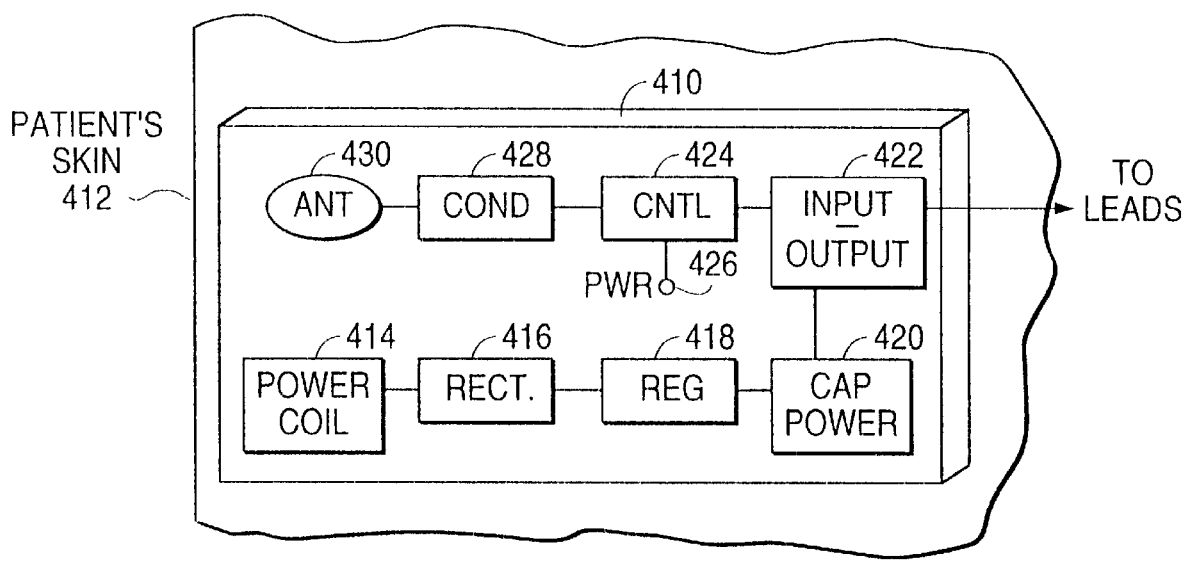

Alternatively, rather than stimulating tissue, an implantable diagnostic device could be utilized to detect the condition of certain bodily organs such as heart or brain. Also, a drug delivery system could be powered capacitive power source 36. In FIG. 6, the diagnostic module would replace stimulator module 422. The electronic pump would replace module 422 if the implant was a drug delivery system.

As described above, the capacitive power source 36 is a high value, small size capacitive energy device comprising a single capacitor or a plurality of parallel connected capacitors having a capacitive rating of at least 0.1 farads and limited in volumetric size to less than 4.0 cubic centimeters.

The refresh-recharge transmitter unit 20 includes a primary battery 70, an ON/OFF switch 72, a low battery light or LED 74, a transmitter electronic module 76, a "stimulator full" light or LED 78, and audible alarm or speaker 80, an RF inductor power coil 82, a modulator/demodulator and decoder 84 and an antenna 21.

In operation, when rechargeable battery 70 is fully charged and ON/OFF switch 72 is on, the refresh-recharge transmitter unit 20 is placed in close proximity to skin 12 and implanted stimulator 10. Inductor coil 82 emits RF waves establishing EMF wave fronts which are received by inductor 30.

Further, transmitter electronic module 76 sends out command signals which are converted by modulator/demodulator decoder 84 and sent via antenna 21 to antenna 11 in the implanted stimulator. These received command signals are demodulated by decoder 44 and replied and responded to based on a program in memory 48 (matched against a "command table" in the memory). Memory 48 then activates the proper control and the inductor receiver coil 30 accepts the RF coupled power from inductor 82.

The RF coupled power, which is alternating current or AC in nature, is converted by the full bridge rectifier circuit 18 into a high DC voltage. Small value capacitor 34 operates to filter and level this high DC voltage at a certain level. Voltage regulator 32 converts the high DC voltage to a lower precise DC voltage while capacitive power source 36 refreshes and replenishes. In a preferred embodiment, approximately 5 coulombs are stored in capacitive power source 36. This is sufficient to power stimulating electronic module 38 for at least 8 hours during the delivery of substantially continual electric stimulation pulses to targeted tissues via implanted leads 52. Longer energy storage times, exceeding 24 hours, are possible dependent upon the value of the capacitor and the power drain due to the continual delivery of stimulation pulses.

When the voltage in capacitive power source 36 reaches a predetermined level (that is, VDD reaches a certain predetermined high level), the high threshold comparator 40 fires and stimulating electronic module 38 sends an appropriate command signal to modulator/decoder 44. Modulator/decoder 44 then sends an appropriate "fully charged" command through antenna 11. This command signal indicating that capacitive power source 36 is fully charged, is received by antenna 21 in the refresh-recharge transmitter unit 20. This "fully charged" command signal is decoded by demodulator/decoder 84 and transmitter electronic module 76 then illuminates the "stimulator full" light or LED 78, an audible alarm is briefly generated by speaker 80, and the RF coupled power transmitted by inductor 82 is turned OFF automatically in order to conserve the power of battery 70.

In the DEMAND mode of operation, when the patient may start or stop stimulation by waving the magnet 14 once near the implant. The magnet emits a magnetic force Lm which pulls reed switch 15 closed. Upon closure of reed switch 15, stimulating electronic module 38 in conjunction with memory 48 begins the delivery (or cessation as the case may be) of controlled electronic stimulation pulses to the targeted tissues near implanted leads 52. In the AUTO mode, stimulation is automatically delivered to the implanted lead based upon programmed ON/OFF times. In a SINGLE mode, stimulation is activated only for the duration of the programmed ON time by waving magnet 14 near the implant. Upon expiration of the ON time, stimulation ceases and the OFF time begins. During this OFF time, further closures of reed switch 15 are ignored.

Figure 2:
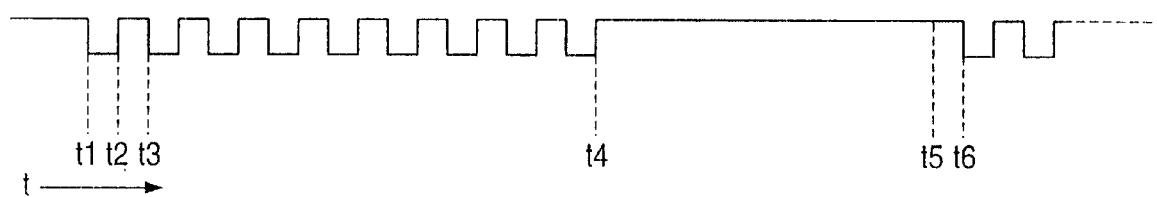
FIG. 2 diagrammatically illustrates a time line showing an example of the substantially continual delivery of stimulation pulses via the implanted stimulator.

FIG. 2 diagrammatically illustrates one type of controlled stimulation pulses. The pulses are classified by pulse width ($t_1$–$t_2$), pulse interval ($t_1$–$t_3$), and pulse amplitude (current level). One frequency cycle is measured from the leading edge of one pulse to the next pulse. Stimulating frequency (PPS) can be calculated by equation 1.

Equation 1:

$$F = \frac{1}{\text{PulseInterval}}$$

The ON time for the entire stimulation pulse train is establish by period $t_1$, through $t_4$. Accordingly, memory 48 stores information regarding the pulse width, pulse amplitude and stimulating frequency, for the delivery of substantially continual stimulation pulses. The patient determines the total ON time identified as time period $t_1$–$t_4$ in FIG. 2. For example at time $t_5$, the patient places magnet 14 near implanted stimulator 10. This closes reed switch 15 and at time $t_6$, the stimulation pulses begin again. Of course, it is important that the physician or medical technician be permitted to change the pulse current frequency, pulse width, and ON/OFF time of the electric stimulation pulses. This is accomplished with programmer unit 16.

Returning to FIG. 1, programmer unit 16 includes keyboard 90, programming circuit 92, rechargeable battery 94 and display 96. Display 96 may include the following elements:

| Display Table | |
|---|---|
| Mode: | Automatic - On Demand - Off |
| Frequency: | Hz (range $n_1$ Hz, to $n_2$ Hz) |
| Current: | mA (range $m_1$ mA to $m_2$ mA) |
| On Time: | minutes maximum |
| Off Time: | minutes maximum |
| Pulse Width: | microseconds |

The physician or medical technician programs programmer unit 16 via keyboard 90. This program regarding the frequency, pulse width, ON time etc. is stored in programming circuit 92. Rechargeable battery 94 enables this programmer unit to be portable. Portability is necessary because antenna 17 in within programmer unit 16 must be placed relatively close to implanted stimulator 10 in order to transfer the commands and programming information from antenna 17 to antenna 11. Upon receipt of this programming data, modulator/demodulator and decoder 44 decodes and conditions these signals and the digital programming information is captured by memory 48. This digital programming information is further processed by stimulating electronic module 38.

As stated earlier, in the DEMAND operating mode, after programming the implanted stimulator, the patient turns ON and OFF the implanted stimulator via hand held magnet 14 and a reed switch 15. In the automatic mode the implanted stimulator turns ON and OFF automatically according to the programmed values for the ON and OFF times.

In one embodiment, the capacitive power source 36 can be recharged or replenished within approximately one hour via the refresh-replenish transmitter unit 20. After the capacitive power source 36 is fully charged, the capacitive power source will enable stimulating electronic module 38 to operate for at least 8 hours before further recharging is necessary. Twenty-four hour operation without recharging or refreshing the capacitive power source is the preferred embodiment. Therefore, since capacitive power source 36 is not subject to "memory loss" common with nickel cadmium rechargeable batteries and not subject to out gassing of obnoxious fumes (common with nickel cadmium batteries), the present invention provides for long service life and lower therapy cost than other comparable implanted stimulators. Further, the patient can easily utilize the implanted stimulator because it is not necessary to continually wear the RF coupled external transmitter for the implanted stimulator to work.

The number of replenish cycles for the capacitive power source 36 and particularly the Panasonic capacitor Model No. 461 is an excess of 100,000 cycles. This exceeds the typical recharge cycle life of a nickel cadmium batteries or other rechargeable chemical battery systems of 500 cycles.

In a preferred embodiment, stimulating electronic module 38 in memory 48 are configured as CMOS units. These components result in a low voltage drain based on the operation of these electronic devices.

When the value of the power source VDD generated by capacitive power source 36 reaches a low level, low threshold comparator 42 fires. This causes stimulating electronic module 38 to go into a "sleep" or wait mode. During the sleep or wait mode, stimulating electric pulses are not delivered to implanted leads 52. The implanted stimulator is "woken up" when refresh-recharge transmitter unit 20 is placed in close proximity to stimulator 10. During this replenish cycle, wake up commands are sent via antenna 21 to antenna 11 and stimulating electronic module 38 is woken up. Simultaneously, as soon as voltage regulator 32 develops an output voltage VDD which exceeds low threshold comparator value 42, the implanted stimulator can immediately begin delivering electric stimulating pulses to the targeted tissue. This ability to replenish and simultaneously deliver stimulating pulses to targeted tissues is unique with respect to the present invention.

The operating principles of an implantable primary or secondary battery powered device and an implantable device powered by a high value capacitive power source are very different. A battery generates energy in a chemical reaction. This energy release or energy storage is accomplished by having two chemically active materials with different electrode potentials present inside the battery. One material serves as the anode which readily gives up electrons and is thus oxidized. Batteries for implantable applications usually employ lithium metal as the anode. The second electrochemically active material in a battery acts as the cathode which accepts electrons and is therefore chemically reduced. Typical implantable battery cathode materials are iodine, silver vanadium oxide, carbon monofluoride and cupric sulfide. External to the battery, transfer to ions between anode and cathode is made possible by the electrolyte which provides high ionic conductivity, but little or no electronic conductivity. A porous separator between the cathode and anode may be used in some batteries to prevent mechanical contact between the anode and the cathode, while allowing electrolyte and ion flow. As a load is applied to the battery, both lithium anode and cathodic material are chemically converted (reacted) to produce a resultant electrical energy until complete depletion of the active materials is achieved. At this point a primarily battery is rendered useless.

In the case of rechargeable battery, both anode and cathode material are recovered back to their original state by recharging the battery. Battery chemistries that are rechargeable are said to have a "reversible reaction." Rechargeable batteries have a limited life since upon recharge, both cathodic and anodic materials are eventually affected. These batteries give off hydrogen upon either charge or discharge, may suffer from a "memory effect" and could explode if shorted. Unlike high value capacitance devices, all rechargeable batteries produce electricity as a result of a chemical reaction. In other words, energy is the by-product of an electrochemical reaction. The general chemical reaction of a nickel-cadmium rechargeable battery is described below in Equation 2.

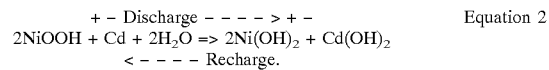

$$+ - \text{Discharge} - - - - > + -$$
$$2\text{NiOOH} + \text{Cd} + 2\text{H}_2\text{O} => 2\text{Ni(OH)}_2 + \text{Cd(OH)}_2$$
$$< - - - - \text{Recharge.}$$

Equation 2

In the high value capacitance power source utilized in the present invention, the principles of operation are purely physical. No chemical reactions are necessary to obtain electrical energy. For example, in a high value capacitance device model such as a double layer capacitor, the charged particles and oriented dipoles that form at the interface of any two phases (solid/solid, solid/liquid, etc.) form a capacitance effect such that the application of an electric field (charge) results in an accumulation of electrostatic charges in a double layer. In essence, the high value capacitance power source serves as an energy storage tank without altering its chemical composition. This principle is defined in the Panasonic product specification for Model 461. It is a pure physical phenomena.

This product specification demonstrates the non-chemical principle of storing and discharging electrical energy. In a high value capacity power source such as the electric double layer capacitors, the electrode material yields a high surface area of around 1000 $m^2$/gram which accounts for it high volumetric efficiency of over 3 farads per cubic inch. Further, unlike batteries the electrodes are non-polar since they are both typically constructed from inert activated carbon mesh. The activated carbon and electrolyte are chemically passive during either charge or discharge mode, hence no chemical reactions or by-products are generated. In addition, the high capacitance power source is safer than batteries since they will not explode or be damaged if short circuited. Unlike conventional electrochemical batteries, the high value capacitance power devices will not manifest anomalies such as charge memory, gas evolution, reactive chemicals, parasitic reactions, heat generation and electrolyte starvation. High value capacitance power sources provide virtually unlimited service life since their electrode system is inert and resistant to electrochemical wear out.

Figure 3:
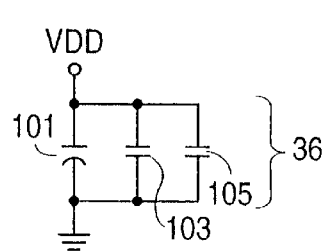
FIG. 3 diagrammatically illustrates one embodiment of the high value, small size capacitive energy storage unit consisting of a plurality of parallel connected capacitors.

FIG. 3 illustrates that capacitive power source 36 can be configured as a polarity of parallel connected capacitors 101, 103 and 105.

Figure 4:
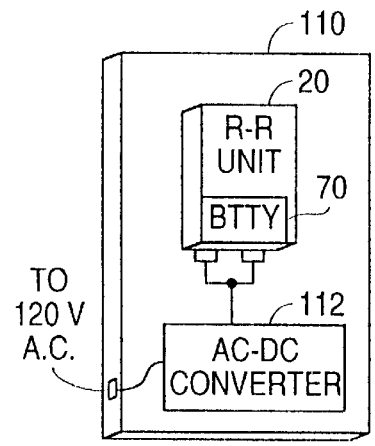
FIG. 4 diagrammatically illustrates a replenish unit for the refresh-recharge transmitter unit.

FIG. 4 diagrammatically illustrates a recharger and an AC-DC converter unit 110 for refresh-replenish unit 20. The refresh-replenish transmitter unit 20 may operate with a rechargeable or primary battery 70 (FIG. 1). This rechargeable battery may be nickel cadmium or other typical recharging battery. However, this rechargeable battery must be periodically recharged. This is accomplished by AC-DC recharging unit 110. Unit 110 is electrically connected to a 120 volt alternating current (AC) power source. Essentially, this 120 volt AC power is converted via converter 112 into a DC voltage. The output of AC-DC converter unit 112 is a DC power signal which is fed to rechargeable battery 70 in the refresh-recharge transmitter unit 20.

Figure 5:
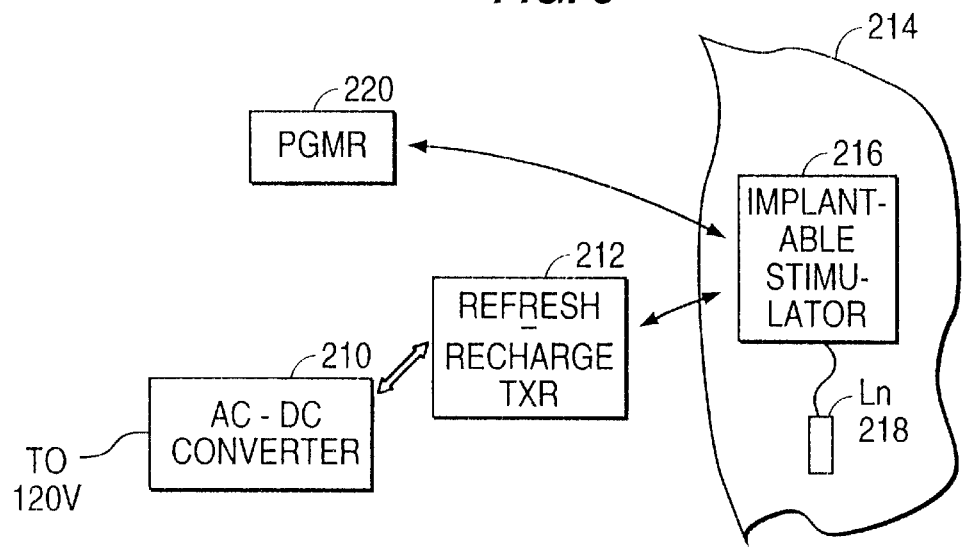
FIG. 5 diagrammatically illustrates the external programmer, external refresh-recharge transmitter, AC-DC converter for the refresh unit and the implanted stimulator; and, FIG. 6 diagrammatically illustrates the major components of the stimulators and other implantable devices.

FIG. 5 diagrammatically illustrates the operation of the present invention in block diagram form. AC-DC converter unit 210 is commonly electrically connected to a 120 volt AC power source. Refresh-replenish transmitter unit 212 is placed in a cradle in the AC-DC converter 210 or is removed therefrom. Upon removal, the refresh-replenish transmitter unit 212 is placed close to skin 214 of the patient. The implantable stimulator 216 then is begins to accept RF coupled power as described above with respect to inductors 82 and 30. Implantable electrodes Ln 218 are placed during surgery next to targeted tissue. When the implanted stimulator 216 must be programmed by the doctor or medical technician, programming unit 220 is placed near skin 214. The programming commands are sent via telemetry to the memory and programmable devices incorporated within implantable stimulator 10.

FIG. 6 diagrammatically illustrates the implantable stimulator in block diagram form. The implantable stimulator 410 is subcutaneously placed in the patient during a surgical procedure. The implantable stimulator 410 is entirely beneath the patient's skin 412. The stimulator includes a power reception coil 414, a full wave rectifier 416, a voltage regulation device 418 and a capacitive power source 420. The inductor power coil, rectifier (rect.) and voltage regulator are necessary to convert the RF coupled power to a constant DC voltage equal to the maximum rated voltage of high value capacitors 420. The output power from capacitive power source 420 is provided to input/output circuit 422. As stated earlier, these stimulators may be neuro stimulators, pacemakers or may be part of a drug delivery system or an RF coupled diagnostic unit. In the event an RF coupled diagnostic unit is utilized, the diagnostic unit would not necessarily stimulate the targeted tissue but rather monitor the electrical activities of that targeted tissue. For example, monitoring EEG and EKG signals is possible. Diagnostic data is obtained from the implant via telemetry.

Implanted device 410 further includes control programming electronics 424 which are further fed with power 426. Power 426 is supplied by capacitive power source 420. A conditioner circuit 428 is interposed between controlled electronics 424 and telemetry antenna 430.

Figure 7:
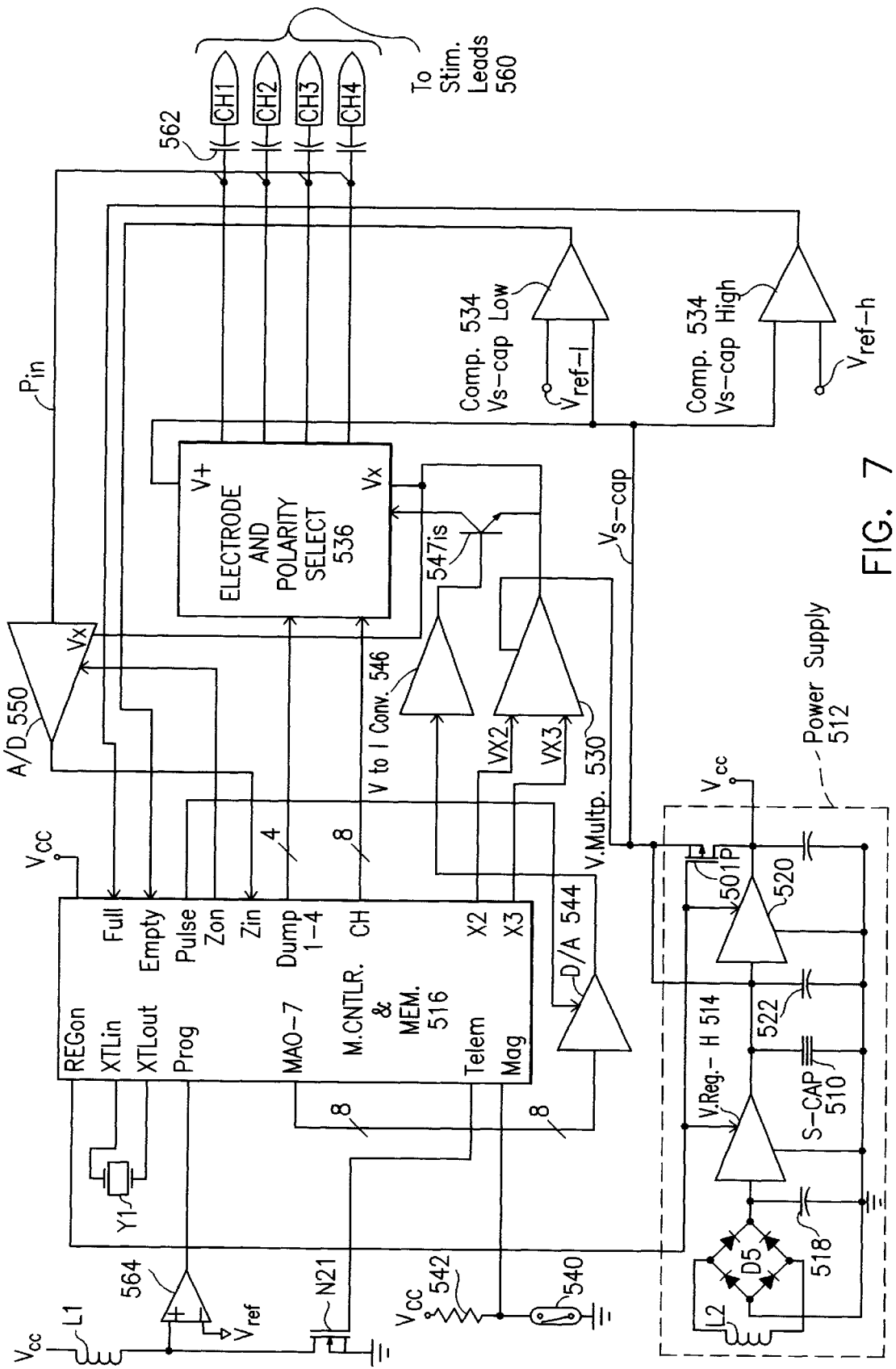
FIG. 7 diagrammatically illustrates a detailed, electronic component diagram of an implant unit which is encased in a titanium enclosure.

FIG. 7 diagrammatically illustrates a detailed, electronic component diagram of an implant unit which is encased in a titanium enclosure. Implant unit is utilized to provide control of electrical stimulation pulses having a certain current and polarity charge which are delivered to nerve or muscle tissue within the human body. These electrode stimulation pulses are utilized to treat elements such as intractable pain, epileptic seizures, urinary incontinence, anal incontinence and peripheral vascular disease. The unit shown in FIG. 7 is powered by a super capacitor S-CAP 510 which is disposed in power supply 512. The entire implant is encased within the titanium casement (not shown) which completely surrounds the implant both electrically and mechanically. The components are diagrammatically illustrated in FIG. 7. In a preferred embodiment, it takes approximately 30 minutes to fully charge the 3 farad super capacitor 510. Once fully charged, the implant unit will operate on a continual basis for approximately 24 hours. This power is supplied exclusively from the energy stored in super capacitor 510.

Power supply 512, shown within the dashed lines in FIG. 7, includes power receiver inductor L2. The output of inductor L2 is applied to a rectifying diode bridge D5. The output of the rectifier is connected to ground at one end and the other end is connected to the input of voltage regulator V.REG.-H. This high voltage regulator 514 outputs a voltage of approximately 5.5 volts. Voltage regulator 514 is turned on and off based upon the output of the microcontroller and memory unit 516. The command is identified in the Microcontroller Port Table (below) as REG-ON. Capacitor 518 provides a filtering mechanism at the input of voltage regulator 514. The output of voltage regulator 514 is also connected to one side of super capacitor 510.

The output of voltage regulator 514 is further applied to a second voltage regulator 520 which is a low voltage regulator. The output of low voltage regulator 520 is approximately 2.0 volts and is identified as $V_{cc}$ in FIG. 7. Capacitor 522 acts as a filter at the input of voltage regulator 520. Voltage regulator 520 is also controlled on and off by microcontroller and memory 516 based upon the status of the command REG-ON.

The power output for super capacitor 510 is identified in FIG. 7 as $V_{s\text{-}cap}$. This voltage is applied to numerous power consumption items such as voltage multiplier 530, comparator 532 (which senses when Vs-cap exceeds a certain voltage level), comparator 534 (which is triggered by a low VS-CAP voltage) and electrode and polarity select unit 536.

Transistor 501P operates in conjunction with the REG-ON signal and the super capacitor voltage VS-CAP.

The Voltage Table which follows lists identifiers for various voltages in the implant.

| Voltage Table | |
|---|---|
| Vs-cap | Voltage at super capacitor +5.5 v |
| Vcc | IC voltage +2.0 v. |
| Vx | Multiplied electrode voltage |
| Vref-l | Low s-cap voltage reference |
| Vref-h | High s-cap voltage reference |

The implant is controlled by microcontroller and memory unit 516. The Microcontroller Port Table which follows lists most of the major ports or terminals from the microcontroller 516.

| Microcontroller Port Table | |
|---|---|
| REG-on | turns voltage regulators on/off |
| XTL-in | oscillator in |
| XTL-out | oscillator out |
| Prog | program input from telemetry unit |
| MAO-7 | output commands 0–7 to drive voltage to current converter |
| Telem | turns telemetry unit on/off |
| Mag | magnetic reed switch open/closed |
| Full | super cap fully charged |
| Empty | super cap voltage below low volt reference |
| Pulse | turns on/off D to A converter for voltage to current converter |
| Zon | release pulse amplitude signal (check stimulation pulse(s)) |
| Zin | pulse amplitude signal check |
| Dump 1–4 | stimulation commands for channels 1–4 |
| CH | positive and negative stimulation commands for channels 1–4 |
| X2 | voltage multiplier factor a |
| X3 | voltage multiplier factor b |

Microcontroller 516 is supplied with timing signals from oscillator Y1. Programming and telemetry transmission signals are applied to the PROG port in microcontroller 516. These programming signals are discussed later. The telemetry input is applied to microcontroller 516 based upon the output of transistor N21. If the patient wishes to activate the implant, he or she can move an electrode magnetic source (typically a magnetic) close to the implant. This crude EMF signal closes reed switch 540. Accordingly, this changes the voltage across resister 542 (acting as a voltage divider) and the command signal is applied to the magnetic reed switch input MAG on the microcontroller 516. Microcontroller 516 generates an 8 bit output MAO-7 to a digital to analog converter 544. The D to A converter is supplied as an input to a voltage to current converter 546. The output of that voltage to current converter is applied to a current source identified as $i_s$ 547. This current signal is feed to electrode and polarity selection unit 536.

Microcontroller and memory 516 is supplied with an IC voltage $V_{cc}$. Command signals are applied to the controller indicating that the super capacitor is fully charged or is empty (signifying a low voltage for VS-CAP). The fully charged command is generated by comparator 532 when VS-CAP reaches a certain high level. This is based upon a reference voltage $V_{rf-h}$. The empty or low voltage signal is generated by comparator 534. This low voltage is referenced against $V_{rf-1}$. The microcontroller generates a pulse command which is applied to digital to analog converter 544. The Zon command is applied to analog to digital converter 550. The A to D converter 550 is utilized to sense the charge and polarity of the stimulation pulses delivered to the patient. The Zon signal is used as a latch to activate A to D converter 550 and the output of A to D converter 550 is applied to microcontroller Zin. Again, the Zin signal is utilized to check the stimulation pulses.

Microcontroller 516 outputs dump signals 1–4 which are applied to electrode and polarity selection unit 536. Also, the microcontroller outputs an 8 bit digital word indicating the channels as well as the polarity for channels 1–4. The channel and polarity signals are applied to electrode and polarity select unit 536. The following table illustrates the 8-bit word applied to unit 536.

| Channel ON and Polarity Table |
| --- |
| Ch1+ |
| Ch1– |
| Ch2+ |
| Ch2– |
| Ch3+ |
| Ch3– |
| Ch4+ |
| Ch4– |

Microcontroller 516 also generates voltage multiplier commands X2 and X3 which are applied to voltage multiplier 530. The output of voltage multiplier 530 is fed to electrode and polarity selection unit 536 as well as A to D converter 550 at input $V_x$. Current stimulating pulses having the correct amplitude, width and polarity are applied to stimulation leads 560 through filtering capacitors, one of which is capacitors 562.

In order to communicate, the implant excites inductor L1 based upon the switching of transistor N21. Transistor N21 is activated based on the telemetry TELEM signal generated by microcontroller 516. One embodiment, transistor N21 is switched on for about 200 microseconds to saturate inductor L1. When transistor N21 is switched OFF, the electric field and inductor L1 collapses thereby inducing a high voltage spike (about 100 volts) across the L1 coil. In one embodiment, the implant communicates with the replenishment unit or the programmer unit based on a pulse width modulated signal sometimes referred to as a pulse interval modulated signal. The Pulse Interval Table that follows shows that a 0 bit pulse width is 5 units "wide" or long induration whereas a 1 bit pulse width occupies 8 units. The 0 bits and 1 bits are separated by interval dividers T2 which are 3 units in width.

| Pulse Interval Table |
| --- |
| T2  T0  T2  T1  T2  T0  T2 |
| . . . . . . 111000001110000000011100000111 . . . . . |
| T0 is zero bit pulse width code |
| T1 is one bit pulse width code |
| T2 is interval divider |

Each transmission of data from the programmer or the replenishment unit to the implant is proceeded by an 8 KHz burst transmission for about 200 milliseconds. Subsequently, the transmitting device generates a command code which identifies the type of action required such as "program", "interrogate" or "measure lead impedance". It is appreciated that there is a serial communications link between the external device (either the replenishment unit or the programmer) and the internal device, that is, the implant.

When high voltage spikes are sensed by inductor L1 in the implant, the signals are filtered, amplified and shaped with appropriate circuitry. This circuitry is identified as a comparator/amplifier 564. Filtration, amplification and shaping of the sensed data signals is known in the art.

In order to transmit data from the implant, transistor N1 is switched on and off which creates voltage spikes across inductor L1. These voltage spikes, configured as EMF signals, are detected, filtered and shaped by the programmer or the replenishment unit as discussed later.

The patient can control some of the functions of the implant unit via the two way, non-invasive EMF communications link between the implant and replenisher unit. Further, the patient can control an on/off cycle by non-invasively activating reed switch 540. With respect to the control by the replenisher unit, the patient can (a) replenish or charge super capacitor 510 within the implant unit; (b) start or stop stimulation based on a telemetric command received by coil L1; (c) adjust the stimulation pulse amplitude again by a telemetric command; and, (d) reprogram the implant and restore the implant to the original stimulation program or schedule based upon a "low voltage" or "empty" signal originating from microcontroller 516 and transmitted to the replenishment unit via telemetry antenna coil L1.

Figure 8:
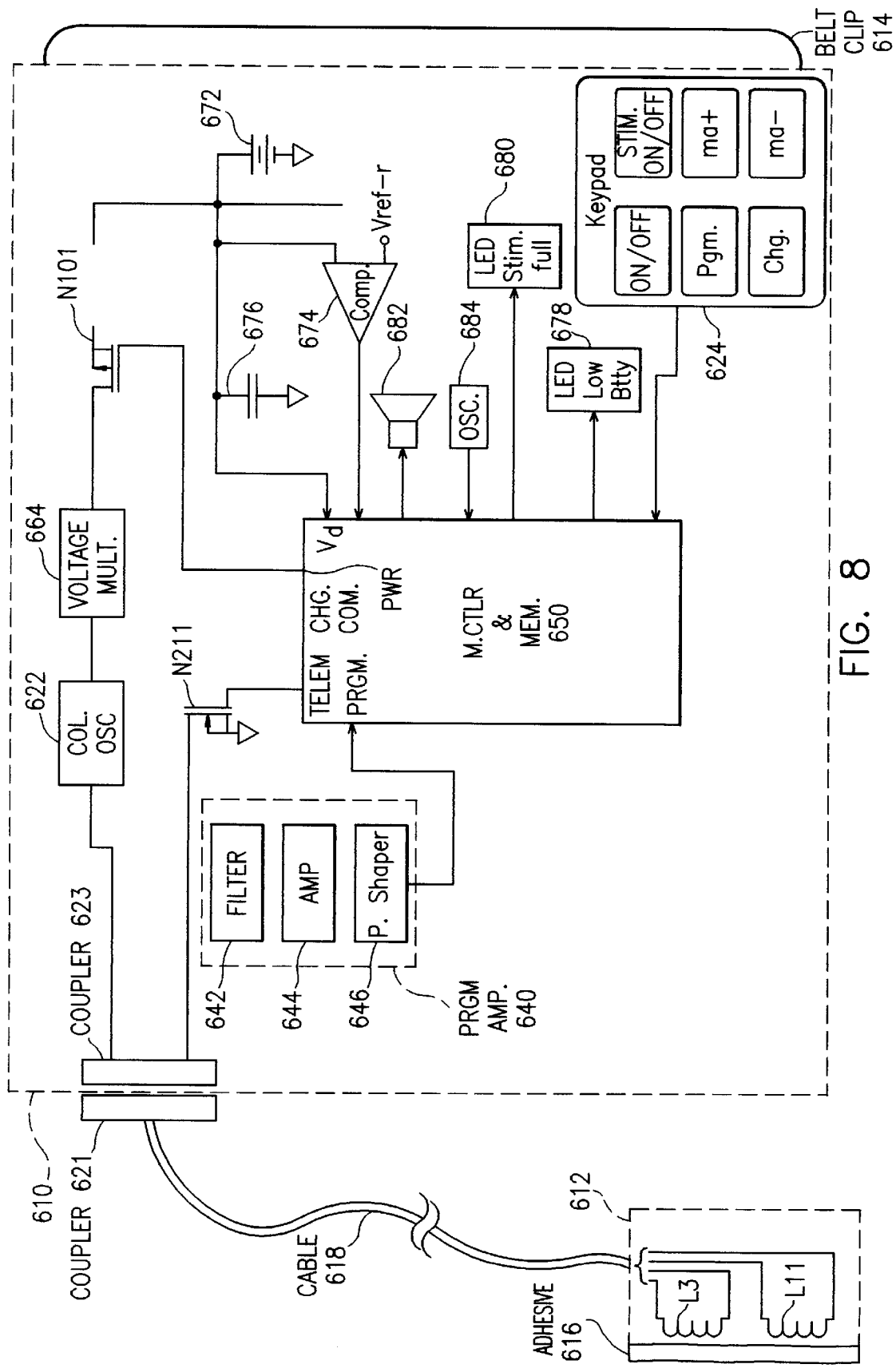
FIG. 8 diagrammatically illustrates a detailed, electronic component diagram of a replenisher unit, part of which is adapted to be carried on a belt of a patient and another part is adapted to be removably adhered to the skin of a patient near the implant.

FIG. 8 illustrates a detailed, electronic component diagram of a replenisher unit. The replenisher unit, in this embodiment, is configured as compact unit 610 and patch unit 612. Compact unit 610 is configured as a relatively thin, rectangular container having a belt clip 614 along one side thereof. The patch unit 612 is a thin, sheet like component having an adhesive 616 along on side thereof. The patch unit 612 is adapted to be placed on the skin of the patient near the implant. Adhesive 616 is utilized to attach patch unit 612 to the skin of the patient. Patch unit 612 is connected via cable 618 to compact unit 610. Cable 618, is, in one embodiment, a 4 wire cable. Mechanical couplers 621 and 623 permit cable 618 to be attached and electrically connected or detached from compact unit 610.

The primary function of the replenisher unit is to periodically and non-invasively replenish the super capacitor in the implant unit. This may be done manually by the patient by pressing the "charge" key on keypad 624 (the CHG key). The Keypad Control Table which follows identifies the major keys and function on keypad 624.

Keypad Control Table

| Key | function |
| --- | --- |
| ON/OFF | replenisher ON or OFF |
| Pgm. | program implant |
| Chg. | charge implant |
| Stim. on/off | initiate or cease stimulation pulses |
| ma+ | increase current amplitude |
| ma− | decrease current amplitude |

The implant, upon detecting a high level voltage VS-CAP at the super capacitor, sends via telemetry a stop charge command to the replenishing unit. Accordingly, the implant and the replenisher interactively determine whether super capacitor is fully charged.

The patient or user can start or stop stimulation current pulses upon depression of the proper keys on keypad 624, can adjust the amplitude of the stimulation pulses and can reprogram the original stimulation schedule or program prescribed by the physician by the depressing the program key on keypad 624.

The replenisher is capable of receiving, decoding and storing a program transmitted by the programmer unit (described later) for later transfer via telemetric communications link to the implant. The replenisher unit is also capable or interrogating the operating values of the stimulation schedule in the implant and to permit the patient to change the pulse amplitude of the stimulation pulses as commanded by the patient. In normal use, the physician will load the same operating stimulation schedule or values into the replenishing unit as well as the implant unit. By storing the stimulation program or schedule into the replenisher unit, the implant can be reprogrammed based upon the program schedule and the replenisher in the event the super capacitor power supply and the implant is not refreshed or recharged in time to prevent memory loss in the implant unit.

Upon manual or automatic activation of the replenishment cycle, the replenishment unit will first interrogate the implant unit to determine the state of the RAM or other memory in the implant. If the super capacitor power supply was permitted to discharge below a minimum memory retention voltage sensed based upon comparator 534 and the value of VS-CAP, the program or stimulation schedule may be lost or corrupted. Upon interrogation by the replenisher unit (via telemetry data transfer), the implant unit will not respond or may respond with inappropriate data representing the stimulation schedule. The replenisher unit will detect this corrupted data storage or program schedule and will commence recharging the super capacitor and after a predetermined charging time (about 5 minutes in one embodiment), the replenisher unit will reinstate the original stimulation program or schedule into the implant.

The replenisher unit utilizes the same pulse interval or pulse width modulation technique described earlier.

In order to transmit data to the implant, transistor N211 is switched on for about 200 microseconds which results in the saturation of inductor coil L11. When transistor N211 is switched off, the electric field in inductor L11 collapses resulting in an induced voltage spike of about 100 volts across the coil. These spikes are detected, filtered and shaped and demodulated by the circuitry within the implant.

High voltage spikes transmitted by the programmer or the implant unit are inductively coupled to inductor L11 within replenisher unit and particularly within the patch unit 612. The received signals are carried by cable 618 through couplers 621 and 623 and are ultimately applied to program amplifier 640. The program amplifier includes a filter 642, and amplifier stage 644 and a pulse shaper stage 646. Ultimately, the filtered, amplified and shaped pulse is applied to the program PRGM input of microcontroller and memory unit 650. The microcontroller and associated memory 650 measures each time of each received pulse, decodes the weight of each signal data byte, composes a byte of the program or telemetrically received digital word and interprets the values for each parameter.

One of the commands sent automatically by the implant is "stop charge" command. Upon receipt and decoding of the stop charge command by microcontroller 650, the replenisher unit ceases charging by cessation of electrode magnetic force waves to the implant.

In order to charge the super capacitor in the implant, inductor coil L3 is activated by a colpitts oscillator 662 which is, in turn, supplied with a charge command from microcontroller 650 as well as an enhanced voltage from voltage multiplier 664. A conventional colpitts oscillator 662 is modified so that it can be turned on or off by microcontroller 560 via transistor N101. When the charge port in microcontroller 650 goes high, the transistors in the colpitts oscillator (not shown) are switched ON. Switching of both transistors pulls one side of a resister down to approximately 30 volts thereby allowing the colpitts oscillator to start oscillation. Likewise, when the charge port of microcontroller 650 goes low, the transistors (not shown) in the colpitts oscillator 662 are turned OFF. When the colpitts oscillator is running, power inductor L3 generates an alternating EMF field which is electromagnetically coupled to inductor L2 within the implant. Therefore, inductors L3 and L2 act as a transformer where L3 is the primary and inductor L2 is the secondary. EMF energy captured by inductor L2 in the implant is rectified and regulated to 5.5 volts in order to charge the super capacitor 510. Voltage multiplier 664 is utilized to convert the battery voltage (approximately 2–3 volts in one embodiment) into approximately 30 volts DC which is required by colpitts oscillator 662. This high voltage is required in order to generate sufficient field strength to reach inductor L2 in the implant. This high voltage and resulting EMF power signal must penetrate the titanium enclosure which encompasses the implant. The replenisher compact unit 610 is powered by a battery 672 which is, in one embodiment, a 3 volt rechargeable battery. The output from the battery is connected to comparator 674 which determines whether the battery has sufficient voltage based upon a reference voltage VREF-R. The replenisher unit also includes a capacitor 767 which is a 1 farad memory back up power storage device. This is another user of a super capacitor. Power is supplied to microcontroller 650 as voltage $V_d$. The output of comparator 674 determines whether battery 672 is low. If it is, microcontroller 650 detects a low battery signal at the output of the comparator. Accordingly, the microcontroller will activate light emitting diode led indicating a low battery. This is done by LED circuit 678. Upon detection of a stimulator full signal transmitted by the implant, microcontroller 650 activates light emitting diode LED which indicates stimulator full. This LED is indicated by circuit 680 in FIG. 8. Additionally, an audible alarm is provided and is diagrammatically illustrated as audible announcer 682. Microcontroller 650 is supplied with timing pulses based upon oscillator 684.

The patient or user can increase or decrease the stimulation pulse amplitudes by depression of the ma+ or ma− keys on keypad 624. In one embodiment, each time one of these push buttons are activated, the stimulation current amplitude will change to the next adjacent up or down value. Any further activation of the switches will be ignored until a pre-determined time period has lapsed. This time window permits the patient to "feel" the effect of the last change of the stimulation current before he or she is allowed to make any further amplitude changes. This prevents excessive over or under stimulation by the patient.

Figure 9:
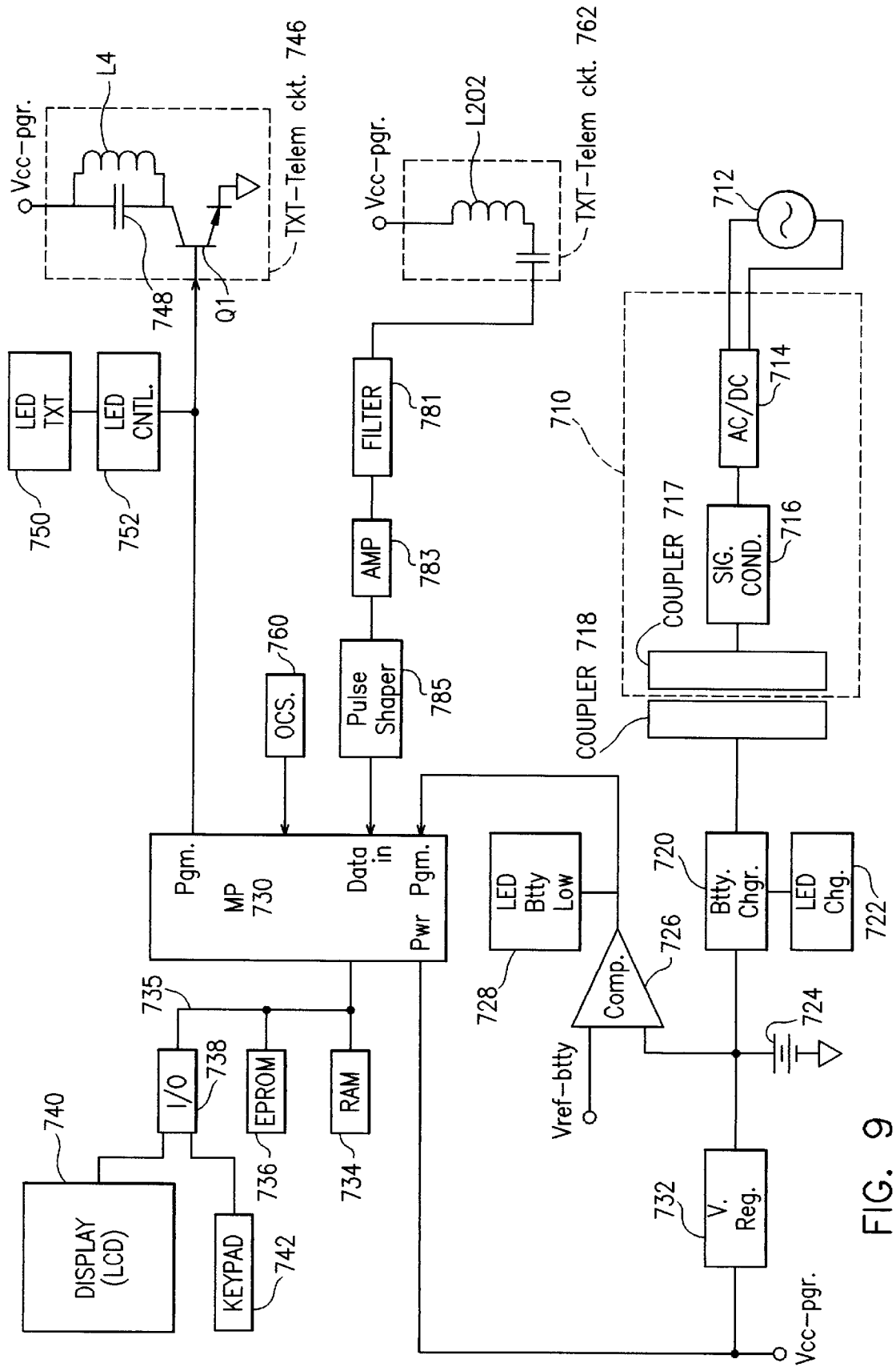
FIG. 9 diagrammatically illustrates a detailed, electronic component diagram of a programmer unit electrically coupled, via mating couplers, to an AC charger and an AC power source.

FIG. 9 illustrates a detailed, electronic component diagram of a programmer unit. Programmer unit normally sits on a cradle 710 which is electrically connected to an AC power source 712. AC power source is converted into a DC voltage by converted 714 and the DC power output is conditioned as appropriate by signal condition 716. The power output from signal conditioner 716 is applied to coupler 717 and mating coupler 718. The power is then applied to a battery charger circuit 720. An LED or lighting emitting diode circuit 722 indicates that the programming is charging battery 724. Battery 724 is, in a preferred embodiment, a nickel cadmium battery having a voltage of 6.2 volts. The output of battery 724 is applied to a comparator 726. Comparator 726 determines whether the voltage from the battery 724 falls below a predetermined voltage level V ref-btty. If so, the output of comparator 726 goes high and an LED circuit 728 is activated and a battery low light is provided. Further, the output of comparator 726 is supplied to a microprocessor 730 in particularly the low battery indicator port on that microprocessor.

The output of battery 724 is further supplied to a voltage regulation circuit 732. The output of the voltage regulations circuit 732. The output of the voltage regulation circuit 732 is the voltage supply for the integrated circuit components of the programmer. This voltage level is identified as V cc-pgr. This voltage is applied to the power input of microprocessor 730. A bus 735 connects a memory identified as RAM 734 and an eprom memory 736. Also, an input output circuit 738 is connected to bus 735. The input output circuit provides an interface between microprocessor 730 and an LCD display unit 740 as well as a keypad unit 742.

The programmer unit transmits telemetry commands by activating a transistor Q1 in the transmit telemetry circuit 746. The telemetry circuit 746 includes a transmission inductor L4 connected in series with transistor Q1. Power is supplied to the other end of the inductor. A capacitor 748 provides a filter for the transmitted signal. Programming activity is identified based upon a light emitting diode or LED 750 controlled by an LED control circuit 752. The LED control circuit is electrically coupled to the programming line leading to transistor Q1 in telemetry circuit 746.

Microprocessor 730 is supplied with timing pulses from oscillator 760.

The programming unit also includes a receiver telemetry circuit 762. Telemetry circuit 762 includes an inductor coil L202. This inductor coil receives signals generated either by the replenisher unit or by the implant. These signals are applied to a filter circuit 781, amplified by amplifier circuits 783 and the amplified signals are shaped by a pulse shaper 785. The resulting pulse width modulated signals are applied to the data in port of microprocessor 730.

The programmer unit transmits telemetry data and signals by switching on and off transistor Q1. The ON-OFF cycle is approximately 200 microseconds. This saturates inductor coil L4. When transistor Q1 is switched off, the electric field collapses and a high voltage spike of about 100 volts appears across inductor L4. This high voltage spike is detected by an inductor within either the implant or the replenisher unit. Each pulse and particularly each pulse interval is measured by the appropriate microcontroller within the implant or the replenisher unit. Accordingly, the telemetry data is decoded by the unit.

In order to confirm that the transmission and decoding and data transmission was error free, the implant unit responds by echoing to the program every bit that you receive. The programmer then compares the echoed values with the intended values. If the two sets of value are equal, the programming unit will then transmit a "transfer" command to the implant. This causes the implant to store the new operating values from a temporary memory storage location into a permanent or operating memory storage location. From that point forward, the implant utilizes that stimulation schedule or program.

It should be noted that a single antenna can be used rather than two antennas as shown in FIG. 9. Two antennas are used in order to improve the programming/telemetry distance.

Figure 10:
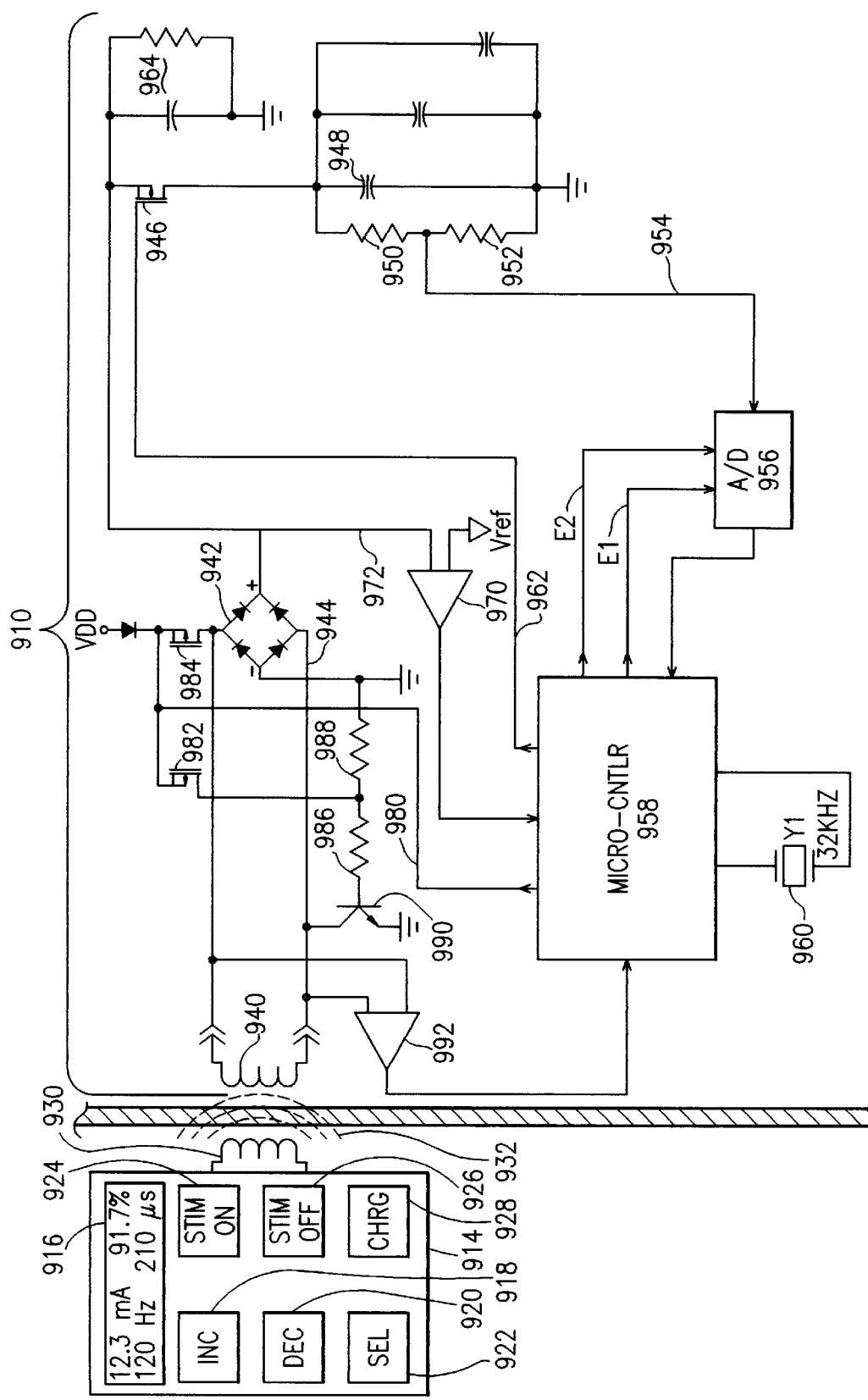
FIG. 10 diagrammatically illustrates another embodiment of a portion of the implant, the surface of the patient's skin and a simplified version of the replenishment unit.

FIG. 10 diagrammatically illustrates a portion of an implant 910, skin surface 912 and replenisher unit 914. The replenisher unit includes a display 916, increase and decrease keys 918, 920, select key 922, stimulation ON key 924, stimulation OFF key 926 and charge key 928. In addition, replenishment unit 914 includes an inductor coil 930. Inductor coil 930 generates either telemetry (data/command) signals or EMF power transmission signals. These signals are schematically illustrated by EMF waves 932.

Portion 910 of the implant includes an inductive coil 940 coupled to a rectifying bridge 942 consisting of four diodes. Diode bridge 942 converts the EMF power transmission signals received by inductive coil 940 from an alternating current into a DC current. This DC current is applied to line 944. Depending upon the state of transistor 946, that DC current is applied to a bank of supercapacitors or the capacitive energy storage unit, one of which is supercapacitor 948. A pair of resistors 950 and 952 are electrically connected across the bank of supercapacitors (which includes capacitor 948). Resistors 950 and 952 form a voltage divider circuit and the voltage level on line 954 represents, in analog form, the voltage charge contained by the bank of supercapacitors. The output of voltage divider circuit 950, 952 is applied to A to D converter 956. The output of A to D converter 956 is applied to microcontroller 958. This digital signal represents the voltage level across the bank of power capacitors. Additionally, a crystal 960 provides timing for the microcontroller or microprocessor 958.

Microcontroller 958 applies a "0" logic signal on line 962 which keeps transistor 946 ON. When transistor 946 is ON, and EMF power transmission signals are being received by inductor coil 940, the capacitors are being charged. The resistive and capacitive circuit 964 is utilized as a filter. Returning to the analog voltage level on line 954, when the output of A to D converter 956 reaches a predetermined high voltage level sensed by an appropriate program in the microcontroller, microcontroller 958 issues a "disconnect replenish" command on line 980. This command also triggers a change in the state of the voltage on line 962 (from 0 to 1) and turns OFF transistor 946 which effectively isolates the rectified DC voltage on line 944 from the supercapacitor bank which includes capacitor 948.

Comparator 970 monitors the charging voltage level on line 972. This voltage level provides an indication when replenishment unit 914 stops its periodic replenishment cycle. In other words, replenishment unit 914 generates EMF power transmission signals not in a continuous manner but in a cyclical manner. For example, EMF power transmissions may be emitted one second ON, one second OFF. Accordingly, the voltage on line 972 can be sensed by the comparator to determine the OFF period for the power replenishment cycle.

Comparator 970 determines when the voltage on line 972 falls below a predetermined voltage level $V_{ref}$. At that time, a signal is applied to the output of comparator 970 and microcontroller 958 has an indication that the replenishment cycle is in an "OFF" cycle portion. At that time, microcontroller 958 can activate a telemetry program to issue a "stop replenishment" command. This stop replenishment command is a digital command applied to line 980. Transistors 982 and 984 modulate the command signal and resistors 986 and 988 in addition to transistor 990 cause a modulated EMF signal to be generated by inductor coil 940. This "stop replenishment" telemetry command is received by inductor coil 930 in replenishment unit 914. The replenishment unit then has an indication to stop the EMF power transmission signals and hence stop charging the supercapacitor bank which includes capacitor 948.

The downlink telemetry signals from unit 914 to the implant are applied through amplifier and filter 992 and ultimately monitored by microcontroller 958.

The "disconnect power" function provided by A to D converter 956 monitoring the analog voltage level on line 954, prevents over-charging of the capacitive power source. Over-charging of the power source may sometimes lead to premature failure of the capacitors which form the capacitor power source.

As the implanted stimulator slowly draws energy from the capacitive power source (capacitor 948), the voltage across the power source decreases proportionally to the rate of discharge. Microcontroller 958 periodically monitors the voltage level on line 954 by activating A to D converter 956. Enabling lines E1 and E2 are used to drive A to D converter 956. When the residual charge level on the capacitive power supply reaches a minimal voltage level, the implanted stimulator will generate a "start replenishment" telemetry command. This telemetry event is described above with respect to the "stop replenishment" command. In the replenisher unit 914, upon detecting the "start replenishment" command, the replenisher unit initiates a new replenishment cycle, that is, generating periodic EMF power transmission signals until the "stop replenishment" command is received by coil 930.

Of course, the implant includes other items not identified in FIG. 10. For example, FIG. 10 does not show an electron and polarity selection unit and the leads to the stimulators as shown in FIGS. 1 and 7. However, the implant would have those components since it must be used to stimulate other organs and tissues in the patient.

The claims appended hereto are meant to cover modifications and changes within the spirit and scope of the present invention.

What is claimed is:

1. A system for delivering electric stimulation pulses, in a controlled manner, to targeted tissue comprising:

an implantable stimulator capable of delivering, in a controlled manner, one or more electric stimulation pulses to targeted tissue;

said implantable stimulator having in its interior:

a power source, contained within said implantable stimulator, sufficient to supply power to said implantable stimulator on an exclusive basis over at least an 8 hour period, said power source including a high value, small size capacitive energy storage unit having a capacitive rating of at least 0.1 farads;

an inductor coil adapted to gather emf power transmissions, a rectifier and a voltage regulator, all electrically coupled to said capacitive energy storage unit and incorporated into said implantable stimulator;

a low level voltage detector, electrically coupled to said capacitive energy source, for detecting and issuing a low voltage command when a voltage at said capacitive energy source falls below a predetermined level, a telemetry circuit coupled to said low voltage detector and receiving said low voltage command, said telemetry circuit transmitting a signal representative of said low voltage command;

means, external to said implantable stimulator and not adapted for implantation, for replenishing said capacitive energy storage unit up to its maximum rated voltage by generating said emf power transmissions near said inductor coil;

said replenishing means having a corresponding telemetry circuit, said corresponding telemetry circuit receiving said signal representative of said low voltage command; and, means for controlling said means for replenishing, said means for controlling coupled to said corresponding telemetry circuit and activating said means for replenishing upon receipt of said signal representative of said low voltage command.

2. A system for delivering electric stimulation pulses as claimed in claim 1 wherein said external means for replenishing and said implantable stimulator include means for checking the exchange of telemetry data and commands therebetween.

3. A system for delivering electric stimulation pulses as claimed in claim 1 wherein said implantable stimulator includes a voltage level detection circuit, coupled to said power source, said voltage level detection circuit having means for determining the voltage across said power source.

4. A system for delivering electric stimulation pulses as claimed in claim 3 wherein said implantable stimulator includes means for electrically decoupling said inductor coil from said power source upon detecting a maximum voltage level from said voltage level detection circuit.

5. A system for delivering electric stimulation pulses, in a controlled manner, to targeted tissue comprising:

an implantable stimulator capable of delivering, in a controlled manner, one or more electric stimulation pulses to targeted tissue;

said implantable stimulator having in its interior:

a power source, contained within said implantable stimulator, sufficient to supply power to said implantable stimulator on an exclusive basis over at least an 8 hour period, said power source including a high value, small size capacitive energy storage unit having a capacitive rating of at least 0.1 farads;

an inductor coil adapted to gather emf power transmissions, a rectifier and a voltage regulator, all electrically coupled to said capacitive energy storage unit and incorporated into said implantable stimulator;

a high level voltage detector, electrically coupled to said capacitive energy source, for detecting and issuing a high voltage command when a voltage at said capacitive energy source exceeds a predetermined level, a telemetry circuit coupled to said high voltage detector and receiving said high voltage command, said telemetry circuit transmitting a signal representative of said high voltage command;

means, external to said implantable stimulator and not adapted for implantation, for replenishing said capacitive energy storage unit up to its maximum rated voltage by generating said emf power transmissions near said inductor coil;

said replenishing means having a corresponding telemetry circuit, said corresponding telemetry circuit receiving said signal representative of said high voltage command; and, means for controlling said means for replenishing, said means for controlling coupled to said corresponding telemetry circuit and deactivating said means for replenishing upon receipt of said signal representative of said high voltage command.

6. A system for delivering electric stimulation pulses as claimed in claim 5 wherein said implantable stimulator includes a voltage level detection circuit, coupled to said power source, said voltage level detection circuit having means for determining the voltage across said power source.

7. A system for delivering electric stimulation pulses as claimed in claim 6 wherein said implantable stimulator includes means for electrically decoupling said inductor coil from said power source upon detecting a maximum voltage level from said voltage level detection circuit.

8. A system for delivering electric stimulation pulses, in a controlled manner, to targeted tissue comprising:

an implantable stimulator capable of delivering, in a controlled manner, one or more electric stimulation pulses to targeted tissue;

said implantable stimulator having in its interior:
a power source, contained within said implantable stimulator, sufficient to supply power to said implantable stimulator on an exclusive basis over at least an 8 hour period, said power source including a high value, small size capacitive energy storage unit having a capacitive rating of at least 0.1 farads;

an inductor coil adapted to gather emf power transmissions, a rectifier and a voltage regulator, all electrically coupled to said capacitive energy storage unit and incorporated into said implantable stimulator;

a low level voltage detector, electrically coupled to said capacitive energy source, for detecting and issuing a low voltage command when a voltage at said capacitive energy source falls below a predetermined level;

a telemetry circuit coupled to said low voltage detector and receiving said low voltage command, said telemetry circuit transmitting a signal representative of said low voltage command; and, a micro-controller with a memory storing a stimulation program and providing means for controlling the delivery of said stimulation pulses based upon said stored stimulation program;

means, external to said implantable stimulator and not adapted for implantation, for replenishing said capacitive energy storage unit up to its maximum rated voltage by generating said emf power transmissions near said inductor coil;

said replenishing means having:
a corresponding telemetry circuit;
a corresponding micro-controller with a memory storing a primary stimulation program for said implantable stimulator;

said corresponding telemetry circuit receiving said signal representative of said low voltage command and passing said representative low voltage signal to said corresponding micro-controller;

said corresponding micro-controller having means for responding to said representative low voltage signal and up loading said primary stimulation program via said corresponding telemetry circuit, said micro-controller controlling said means for replenishing said capacitive energy storage unit up to its maximum rated voltage and activating the same upon receipt of said representative low voltage signal.

9. A system for delivering electric stimulation pulses as claimed in claim 8 wherein said external means for replenishing includes a user actuable control and means to generate increase or diminish stimulation pulse commands based upon user actuation of said user actuable control, and said corresponding micro-controller having means to transfer said increase or diminish stimulation pulse commands to the implant micro-controller via said telemetry circuits, said implant micro-controller having means for altering said stimulation program based upon said increase or diminish stimulation pulse commands.

10. A system for delivering electric stimulation pulses as claimed in claim 9 wherein said external means for replenishing and said implantable stimulator include means for checking the exchange of telemetry data and commands therebetween, the respective means for checking utilizing said implant micro-controller and memory and said corresponding micro-controller and memory in said means for replenishing.

11. A system for delivering electric stimulation pulses as claimed in claim 8 wherein said external means for replenishing includes, as part of said corresponding micro-controller and memory, means to interrogate said implant micro-controller and memory in order to ascertain the validity of said stimulation program stored therein.

12. A system for delivering electric stimulation pulses as claimed in claim 11 wherein said means to interrogate includes means to re-program said implant micro-controller and memory upon detection of an invalid stimulation program.

13. A system for delivering electric stimulation pulses as claimed in claim 11 wherein, said implantable stimulator includes:
a high level voltage detector, electrically coupled to said capacitive energy source, for detecting and issuing a high voltage command when a voltage at said capacitive energy source exceeds a predetermined high level; and, said telemetry circuit includes means to transmit a signal representative of said high voltage command; and, said means for replenishing includes:
means, as part of said means for controlling, for deactivating said means for replenishing upon receipt of said signal representative of said high voltage command.

14. A system for delivering electric stimulation pulses as claimed in claim 8 wherein said implantable stimulator includes a voltage level detection circuit, coupled to said power source, said voltage level detection circuit having means for determining the voltage across said power source.

15. A system for delivering electric stimulation pulses as claimed in claim 14 wherein said implantable stimulator includes means for electrically decoupling said inductor coil from said power source upon detecting a maximum voltage level from said voltage level detection circuit.

16. A method of providing, on an exclusive basis, power to an implantable stimulator during at least an 8 hour cycle of substantially continual delivery of one or more electric stimulation pulses to targeted tissue in a controlled manner comprising the steps of:

incorporating and containing a capacitive device in said implantable stimulator, said capacitive device having a capacitive rating of at least 0.1 farads;

capturing at least 5 coulombs of electrical energy in said capacitive device prior to said 8 hour period;

powering said implantable stimulator during said 8 hour cycle and the substantially continual delivery of electric stimulation pulses solely from said capacitive device;

permitting the automatic re-programming of said implantable stimulator upon detection of a corrupted stimulation program in said stimulator.

17. A method as claimed in claim 16 including the steps of automatically beginning and ending a replenishment cycle for said capacitive device upon detection of low and high voltage levels, respectively.

* * * * *